(12) United States Patent
Morton

(10) Patent No.: US 9,158,027 B2
(45) Date of Patent: Oct. 13, 2015

(54) MOBILE SCANNING SYSTEMS

(75) Inventor: Edward James Morton, Guildford (GB)

(73) Assignee: Rapiscan Systems, Inc., Torrance, CA (US)

( * ) Notice: Subject to any disclaimer, the term of this patent is extended or adjusted under 35 U.S.C. 154(b) by 934 days.

(21) Appl. No.: 12/919,483

(22) PCT Filed: Feb. 27, 2009

(86) PCT No.: PCT/GB2009/000556
§ 371 (c)(1),
(2), (4) Date: Dec. 27, 2010

(87) PCT Pub. No.: WO2009/106847
PCT Pub. Date: Sep. 3, 2009

(65) Prior Publication Data
US 2011/0098870 A1    Apr. 28, 2011

(30) Foreign Application Priority Data
Feb. 28, 2008    (GB) .................................. 0803643.6

(51) Int. Cl.
*G01V 5/00* (2006.01)
*G01N 23/04* (2006.01)
(52) U.S. Cl.
CPC .............. *G01V 5/0016* (2013.01); *G01N 23/04* (2013.01); *G01V 5/0083* (2013.01)
(58) Field of Classification Search
USPC .......................................................... 701/2
See application file for complete search history.

(56) References Cited

U.S. PATENT DOCUMENTS

| | | |
|---|---|---|
| 2,831,123 A | 4/1958 | Daly |
| 3,766,387 A | 10/1973 | Heffan et al. |
| 3,770,955 A | 11/1973 | Tomita et al. |
| 3,784,837 A | 1/1974 | Holmstrom |
| RE28,544 E | 9/1975 | Stein et al. |
| 4,047,035 A | 9/1977 | Dennhoven et al. |
| 4,139,771 A | 2/1979 | Dennhoven et al. |
| 4,210,811 A | 7/1980 | Dennhoven et al. |
| 4,216,499 A | 8/1980 | Kunze et al. |
| 4,366,382 A | 12/1982 | Kotowski |
| 4,430,568 A | 2/1984 | Yoshida et al. |
| 4,566,113 A | 1/1986 | Donges et al. |
| 4,599,740 A | 7/1986 | Cable |
| 4,626,688 A | 12/1986 | Barnes |
| 4,641,330 A | 2/1987 | Herwig et al. |
| 4,709,382 A | 11/1987 | Sones |
| 4,736,401 A | 4/1988 | Donges et al. |
| 4,788,704 A | 11/1988 | Donges et al. |
| 4,817,123 A | 3/1989 | Sones et al. |
| 4,825,454 A | 4/1989 | Annis et al. |
| 4,872,188 A | 10/1989 | Lauro et al. |

(Continued)

FOREIGN PATENT DOCUMENTS

| | | |
|---|---|---|
| EP | 0287707 | 11/1982 |
| EP | 0176314 | 4/1986 |

(Continued)

*Primary Examiner* — Shelley Chen
(74) *Attorney, Agent, or Firm* — Novel IP

(57) ABSTRACT

A mobile scanning system with a scanner including a radiation source and detectors mounted on a vehicle and arranged to scan an object, a controller mounted on the vehicle and arranged to control the scanner, an operator system arranged to be located remote from the vehicle and to communicate with the controller to enable an operator to interact remotely with the controller.

19 Claims, 3 Drawing Sheets

(56) References Cited

U.S. PATENT DOCUMENTS

| | | | |
|---|---|---|---|
| 4,884,289 | A | 11/1989 | Glockmann et al. |
| 4,979,202 | A | 12/1990 | Siczek et al. |
| 4,991,189 | A | 2/1991 | Boomgaarden et al. |
| 5,022,062 | A | 6/1991 | Annis |
| 5,065,418 | A | 11/1991 | Bermbach et al. |
| 5,091,924 | A | 2/1992 | Bermbach et al. |
| 5,098,640 | A | 3/1992 | Gozani et al. |
| 5,179,581 | A | 1/1993 | Annis |
| 5,181,234 | A | 1/1993 | Smith |
| 5,182,764 | A | 1/1993 | Peschmann et al. |
| 5,221,843 | A | 6/1993 | Alvarez |
| 5,224,144 | A | 6/1993 | Annis |
| 5,237,598 | A | 8/1993 | Albert |
| 5,247,561 | A | 9/1993 | Kotowski |
| 5,253,283 | A | 10/1993 | Annis et al. |
| 5,313,511 | A | 5/1994 | Annis et al. |
| 5,367,552 | A | 11/1994 | Peschmann |
| 5,379,334 | A | 1/1995 | Zimmer et al. |
| 5,493,596 | A | 2/1996 | Annis |
| 5,548,123 | A | 8/1996 | Perez-Mendez et al. |
| 5,638,420 | A | 6/1997 | Armistead |
| 5,642,393 | A | 6/1997 | Krug et al. |
| 5,642,394 | A | 6/1997 | Rothschild |
| 5,666,393 | A | 9/1997 | Annis |
| 5,687,210 | A | 11/1997 | Maitrejean et al. |
| 5,692,028 | A | 11/1997 | Geus et al. |
| 5,751,837 | A | 5/1998 | Watanabe et al. |
| 5,764,683 | A | 6/1998 | Swift et al. |
| 5,768,334 | A | 6/1998 | Maitrejean et al. |
| 5,787,145 | A | 7/1998 | Geus |
| 5,805,660 | A | 9/1998 | Perion et al. |
| 5,838,759 | A | 11/1998 | Armistead |
| 5,903,623 | A | 5/1999 | Swift et al. |
| 5,910,973 | A | 6/1999 | Grodzins |
| 5,930,326 | A | 7/1999 | Rothschild et al. |
| 5,940,468 | A | 8/1999 | Huang et al. |
| 5,974,111 | A | 10/1999 | Krug et al. |
| 6,031,890 | A | 2/2000 | Bermbach et al. |
| 6,058,158 | A | 5/2000 | Eiler |
| 6,067,344 | A | 5/2000 | Grodzins et al. |
| 6,081,580 | A | 6/2000 | Grodzins et al. |
| 6,094,472 | A | 7/2000 | Smith |
| 6,151,381 | A | 11/2000 | Grodzins et al. |
| 6,188,747 | B1 | 2/2001 | Geus et al. |
| 6,192,101 | B1 | 2/2001 | Grodzins |
| 6,192,104 | B1 | 2/2001 | Adams |
| 6,195,413 | B1 | 2/2001 | Geus et al. |
| 6,198,795 | B1 | 3/2001 | Naumann et al. |
| 6,218,943 | B1 | 4/2001 | Ellenbogen |
| 6,249,567 | B1 | 6/2001 | Rothschild et al. |
| 6,252,929 | B1 | 6/2001 | Swift et al. |
| 6,256,369 | B1 | 7/2001 | Lai |
| 6,278,115 | B1 | 8/2001 | Annis et al. |
| 6,282,260 | B1 | 8/2001 | Grodzins |
| 6,292,533 | B1 | 9/2001 | Swift et al. |
| 6,301,326 | B2 | 10/2001 | Bjorkholm |
| 6,320,933 | B1 | 11/2001 | Grodzins et al. |
| 6,356,620 | B1 | 3/2002 | Rothschild et al. |
| 6,424,695 | B1 | 7/2002 | Grodzins et al. |
| 6,434,219 | B1 | 8/2002 | Rothschild et al. |
| 6,435,715 | B1 | 8/2002 | Betz et al. |
| 6,442,233 | B1 | 8/2002 | Grodzins et al. |
| 6,445,765 | B1 | 9/2002 | Frank et al. |
| 6,453,003 | B1 | 9/2002 | Springer et al. |
| 6,453,007 | B2 | 9/2002 | Adams et al. |
| 6,456,684 | B1 | 9/2002 | Mun et al. |
| 6,459,761 | B1 | 10/2002 | Grodzins et al. |
| 6,459,764 | B1 | 10/2002 | Chalmers et al. |
| 6,473,487 | B1 | 10/2002 | Le |
| RE37,899 | E | 11/2002 | Grodzins et al. |
| 6,483,894 | B2 | 11/2002 | Hartick et al. |
| 6,507,025 | B1 | 1/2003 | Verbinski et al. |
| 6,532,276 | B1 | 3/2003 | Hartick et al. |
| 6,542,574 | B2 | 4/2003 | Grodzins |
| 6,542,578 | B2 | 4/2003 | Ries et al. |
| 6,542,580 | B1 | 4/2003 | Carver et al. |
| 6,546,072 | B1 | 4/2003 | Chalmers |
| 6,552,346 | B2 | 4/2003 | Verbinski et al. |
| 6,563,903 | B2 | 5/2003 | Kang et al. |
| 6,580,778 | B2 | 6/2003 | Meder |
| 6,584,170 | B2 | 6/2003 | Aust et al. |
| 6,597,760 | B2 | 7/2003 | Beneke et al. |
| 6,606,516 | B2 | 8/2003 | Levine |
| 6,636,581 | B2 | 10/2003 | Sorenson |
| 6,653,588 | B1 | 11/2003 | Gillard-Hickman |
| 6,658,087 | B2 | 12/2003 | Chalmers et al. |
| 6,663,280 | B2 | 12/2003 | Doenges |
| 6,665,373 | B1 | 12/2003 | Kotowski et al. |
| 6,665,433 | B2 | 12/2003 | Roder |
| 6,763,635 | B1 | 7/2004 | Lowman |
| 6,785,357 | B2 | 8/2004 | Bernardi et al. |
| 6,812,426 | B1 | 11/2004 | Kotowski et al. |
| 6,816,571 | B2 | 11/2004 | Bijjani et al. |
| 6,837,422 | B1 | 1/2005 | Meder |
| 6,839,403 | B1 | 1/2005 | Kotowski et al. |
| 6,843,599 | B2 | 1/2005 | Le et al. |
| 6,920,197 | B2 | 7/2005 | Kang et al. |
| 7,039,159 | B2 | 5/2006 | Muenchau et al. |
| 7,166,844 | B1 | 1/2007 | Gormley et al. |
| 7,207,713 | B2 | 4/2007 | Lowman |
| 7,500,931 | B2 * | 3/2009 | Rosemeier et al. ............. 475/5 |
| 2004/0086078 | A1 | 5/2004 | Adams et al. |
| 2004/0125914 | A1 * | 7/2004 | Kang et al. ................ 378/57 |
| 2004/0141584 | A1 | 7/2004 | Bernardi et al. |
| 2004/0258198 | A1 * | 12/2004 | Carver et al. ............. 378/57 |
| 2005/0117700 | A1 | 6/2005 | Peschmann |
| 2005/0156734 | A1 | 7/2005 | Zerwekh et al. |
| 2005/0169421 | A1 | 8/2005 | Muenchau et al. |
| 2007/0087885 | A1 * | 4/2007 | Rosemeier et al. ............. 475/5 |
| 2007/0110215 | A1 | 5/2007 | Hu et al. |
| 2007/0151783 | A1 * | 7/2007 | Yamauchi .................. 180/65.3 |
| 2007/0269005 | A1 | 11/2007 | Chalmers et al. |
| 2007/0280416 | A1 | 12/2007 | Bendahan et al. |
| 2007/0280502 | A1 | 12/2007 | Paresi et al. |
| 2008/0044801 | A1 | 2/2008 | Modica et al. |
| 2008/0123809 | A1 * | 5/2008 | Tudor et al. ................ 378/57 |
| 2008/0156992 | A1 * | 7/2008 | Kang et al. ............. 250/359.1 |

FOREIGN PATENT DOCUMENTS

| | | |
|---|---|---|
| WO | WO2006/036076 | 4/2006 |
| WO | WO2006/045019 | 4/2006 |
| WO | WO2006/078691 | 7/2006 |
| WO | WO2007/051092 | 5/2007 |
| WO | WO2009/106847 | 9/2009 |

* cited by examiner

MOBILE SCANNING SYSTEMS

CROSS REFERENCE

The present application is a national stage application of PCT/GB2009/000556, filed on Feb. 27, 2009, which further relies on Great Britain Patent Application Number 0803643.6, filed on Feb. 28, 2008, for priority. The aforementioned applications are herein incorporated by reference in their entirety.

FIELD OF THE INVENTION

The present invention relates to scanning systems. It has particular application in scanning systems for cargo, but can also be used in scanners for other applications.

BACKGROUND

There exists a requirement for screening of cargo items for detection of illicit materials and devices. One class of screening device comprises a truck platform upon which is mounted a high energy X-ray linear accelerator and a series of X-ray detectors. The X-ray detectors are advantageously mounted on a hydraulically operated boom so that the system can be deployed to form a scanning system.

When an object is to be inspected, the entire truck is driven past the stationary object such that the object passes through the X-ray beam between the X-ray source and the X-ray detector array. X-ray projection data is built up line-by-line to form a two-dimensional image.

A mobile truck screening system typically comprises a standard truck chassis with integral drivers cab. Built onto the flat bed at the back of the truck is an inspectors cab and the X-ray imaging device which typically comprises a hydraulically operated boom and X-ray linear accelerator. There is typically an operational exclusion zone around the truck during the scanning process to reduce the X-ray exposure to personnel in the vicinity of the screening area to an acceptable level. A typical exclusion zone dimension is around 30 m×30 m.

The inspectors pod is typically formed from dense materials such as steel and lead so that radiation which is scattered from the object under inspection is attenuated to result in a dose to the inspector that is of an acceptable level. The inspector is usually involved in reviewing image data to verify the presence or otherwise of illicit materials or devices in the cargo load. The inspector may also be involved in operation of the truck system, for example in scanning manifest information or monitoring of the technology that is used on the truck itself.

SUMMARY OF THE INVENTION

The present invention provides a mobile scanning system comprising a scanner including a radiation source and detection means, such as detectors, mounted on a vehicle and arranged to scan an object, control means, such as a controller, mounted on the vehicle and arranged to control the scanner, an operator system arranged to be located remote from the vehicle and to communicate with the control means to enable an operator to interact remotely with the control means.

The operator system may be arranged to communicate wirelessly with the control means, or by an electrical or optical link.

The scanner may be arranged to generate scan data when scanning an object, and the control means may be arranged to communicate the scan data to a monitoring system. The monitoring system may arranged to generate an image from the scan data, and may include display means to display the image. The monitoring system may be co-located with, or form a part of, the operator system. Alternatively it may be remote from the operator system. This can allow the monitoring system to receive image data from a plurality if different scanners.

The present invention therefore further comprises a scanning system comprising a plurality of scanners according to the invention and a monitoring system arranged to receive image data from each of the scanning systems.

The control means, such as a controller, may be arranged to receive signals from the operator system and/or one or more sensing systems. The control means may be arranged to control the scanner or the vehicle, or a support system supporting the scanner on the vehicle, in response to the signals. For example the control means may be arranged to control at least one of starting and stopping of the scanner in response to the signals, or other parameters of the scanning process. The control means may be arranged to control at least one of the speed and steering of the vehicle in response to the signals. For example the control means may be arranged to detect obstacles and to control the vehicle or the scanner support so as to avoid any detected obstacles.

An aim of some embodiments of the present invention is to provide a system for operation of such truck based X-ray scanners that minimises the weight of the truck, reduces operator dose and reduces scanning times.

In some embodiments of the present invention, the inspectors pod is removed from the truck platform and re-sited to a safe area outside the normal operating exclusion zone. A wireless network link may be established between the mobile truck and the stationary inspectors' cabin. This wireless link may be designed to carry imaging data and operational data from the truck itself to allow remote inspection of cargo data. The operator system may be arranged to transmit the imaging data on to a separate monitoring system which can include workstations where workers can review and analyse the images of the scanned items. Alternatively the system controller can be arranged to transmit the image data direct to a separate monitoring system.

Preferred embodiments of the present invention will now be described by way of example only with reference to the accompanying drawings.

DESCRIPTION OF THE PREFERRED EMBODIMENTS

Figure 1:
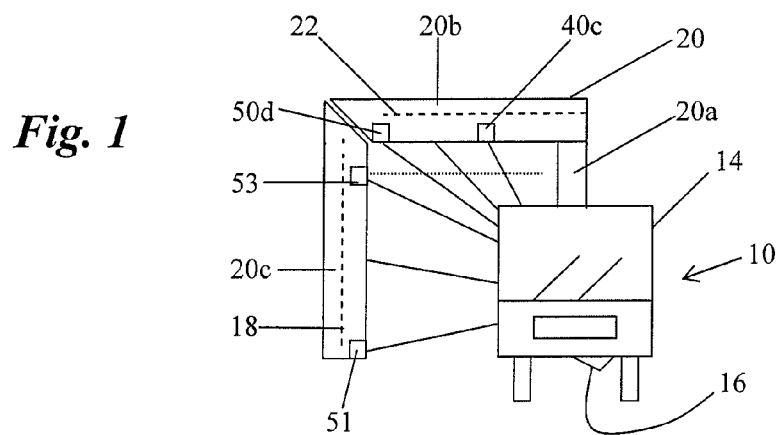
FIG. 1 is a front view of a vehicle forming part of a mobile scanning system according to an embodiment of the invention.
Figure 2:
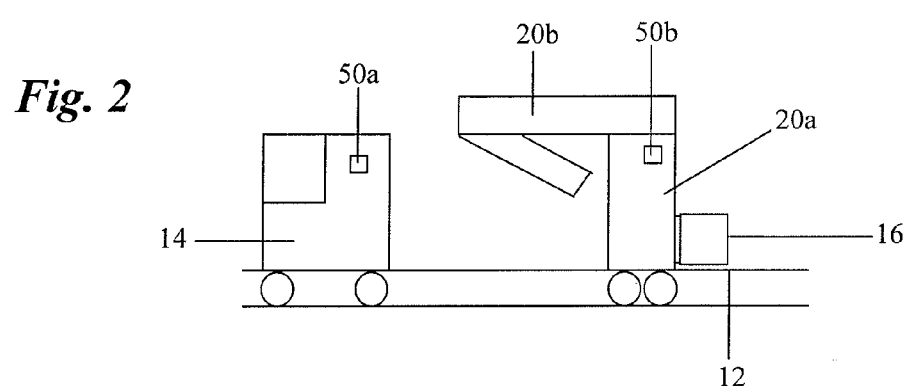
FIG. 2 is a side view of the vehicle of FIG. 1.

Referring to FIGS. 1 and 2, a vehicle 10 forming part of a scanning system according to an embodiment of the invention comprises a chassis 12 supporting a driver's cab 14, an X-ray source in the form of a linear accelerator (linac) 16, and an X-ray detector array 18 supported on a hydraulically operated detector boom 20. The boom 20 comprises a vertical support section 20a rigidly fixed at a first end to the vehicle chassis 12, a horizontal detector section 20b and a vertical detector section 20c. The horizontal detector section 20b is pivotally mounted on the top of the support section 20a so that it can pivot about a vertical axis to swing between a stowed position parallel with the longitudinal axis of the vehicle, and a deployed position as shown in FIG. 1 in which it projects laterally from the side of the vehicle. The vertical detector section 20c is pivotally mounted on the second end of the horizontal section 20b so that it can swing from a stowed position as shown in FIG. 2 down into a vertical deployed position as shown in FIG. 1. The two detector sections 20b, 20c each support linear array of X-ray detectors 22, the arrays being horizontal and vertical respectively when the boom 20 is deployed, making up the complete array 18. The linac 16 is mounted on the vehicle close to the base of the support section 20a and is arranged to produce a fan beam of X-rays upwards and laterally in a scanning plane towards the two detector arrays.

In a modification to this embodiment the X-ray source can be mounted at the bottom of the vertical boom section 20c furthest from the vehicle, and the detectors be mounted on the horizontal boom section 20b and the support section 20a which is directly mounted on the vehicle.

Figure 3:
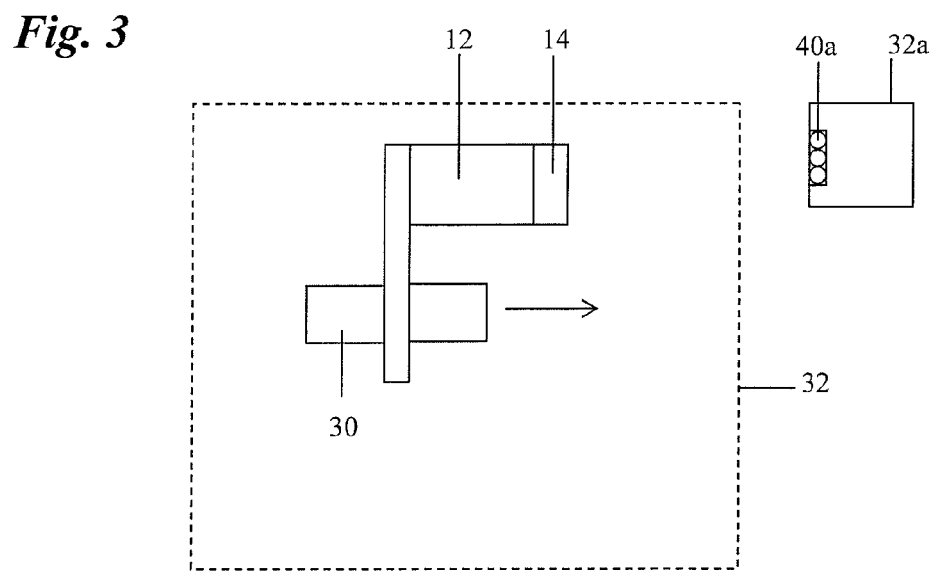
FIG. 3 is a plan view of a scanning system including the vehicle of FIG. 1.

Referring to FIG. 3, when the vehicle 10 is being used to perform a scan, for example of a cargo container 30, it is placed within an exclusion zone 32, from which people are excluded for their own protection during scanning.

Figure 4:
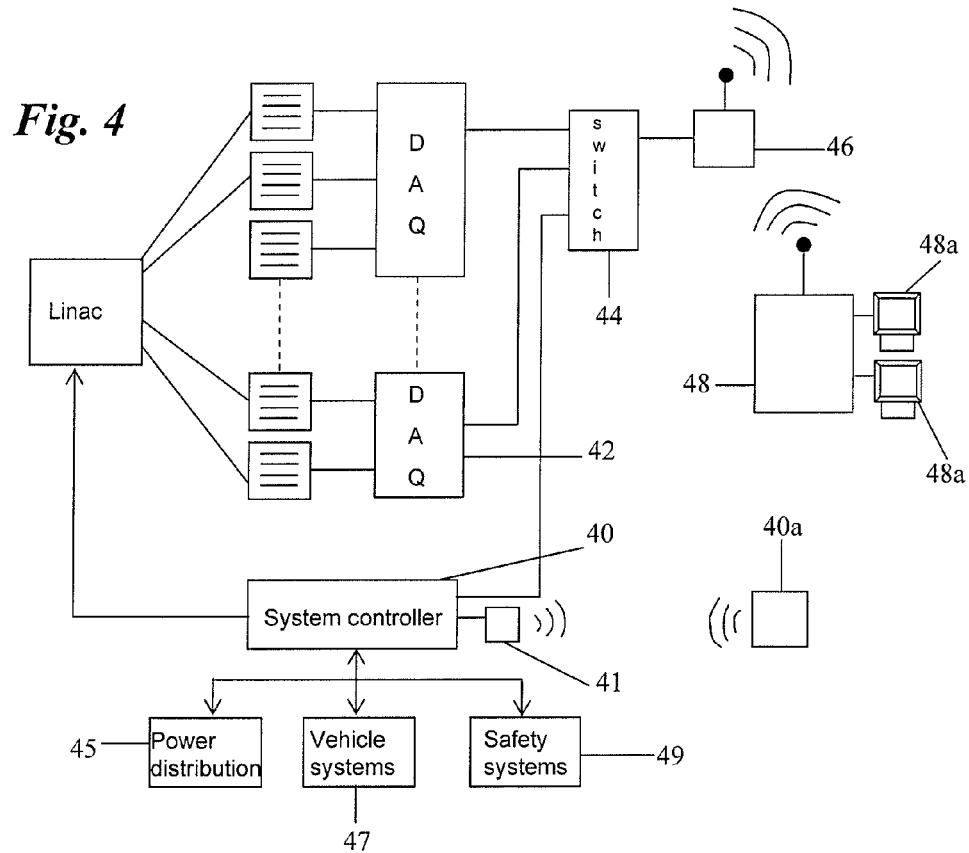
FIG. 4 is a schematic diagram of the system of FIG. 3.

Referring to FIG. 4, a system controller 40 is arranged to control the linac 16 to produce pulses of X-rays. In this embodiment the linac is arranged to produce an X-ray spectrum with a peak energy of at least 900 keV, and preferably at least 1 Mev. The linear detectors of both of the arrays are connected to a data acquisition system 42 which is connected to a network switch 44 which in turn is connected to a wireless network access point 46. The X-ray imaging system is driven by the system controller 40 which determines the timing between the linac X-ray pulses and the data acquisition system 42. Data from the data acquisition system 42 is formatted into Ethernet packets which are then passed through the network switch 44 to the wireless access point 46 for onward transmission to an external monitoring station 48 comprising one or more imaging workstations 48a at which workers can review and analyse the scan images to determine whether the scanned items represent a threat. The monitoring station 48 is part of a distributed scanning system comprising a number of other scanning vehicles each of which can be used at different locations and each of which is arranged to transmit its scan data to the monitoring station for analysis. This enables the skilled personnel who perform the analysis of the scan images to be located together, and their time to be efficiently allocated to different tasks.

The system controller 40 also manages major sub-systems of the system including power distribution 45, vehicle systems 47 and safety systems 49. The system controller 40 is also arranged to communicate wirelessly by means of a wireless transmitter/receiver 41 with a remote control station 40a which is located in an inspector's pod 32a which is outside the exclusion zone 32. The control station 40a has a number of user inputs 40b which can be used by an inspector to further control the scanning process. These user inputs 40b are arranged to cause the control station 40a to emit signals to the system controller, including for example a start signal to start an automatic scan, and stop signal to stop the scan. These enable the inspector to start and stop the scanning process which can proceed under the control of the system controller 40.

By removing the inspector's pod from the system, the total weight can be reduced significantly and dose to the inspectors who would previously have been located in an inspector's cabin on the vehicle has now been eliminated. There is no loss in functionality of the system.

Figure 5:
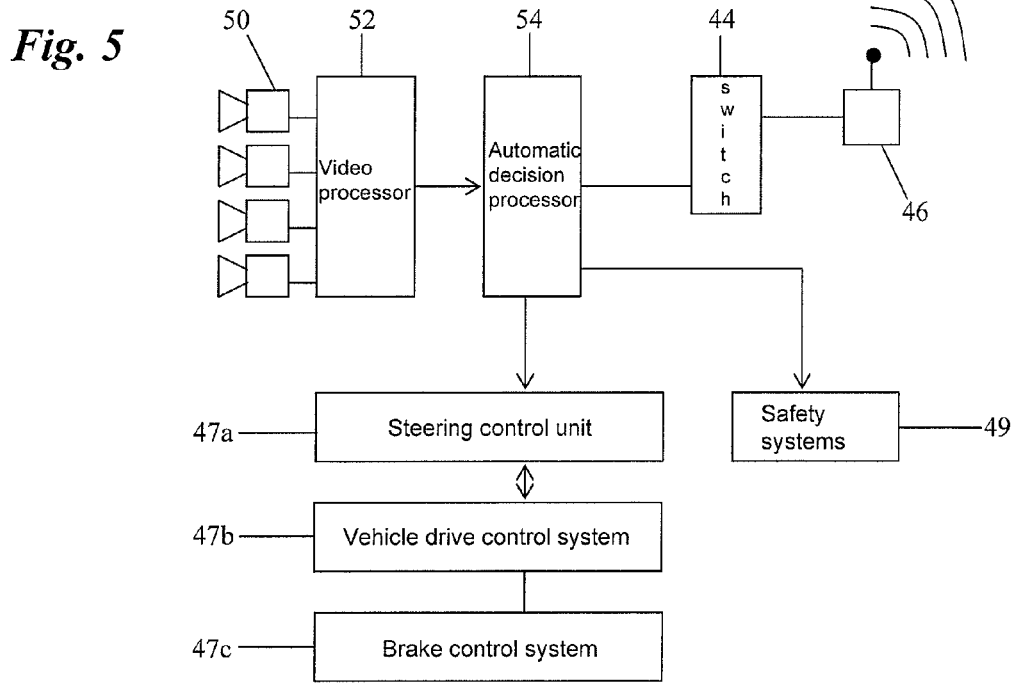
FIG. 5 is a schematic diagram of a control system of the vehicle of FIG. 1.

Referring to FIG. 5, in a second aspect of the invention, and in this embodiment, a remote driving system is included, This system can advantageously use video technology to steer and control the operation of the system. The remote driving system comprises an array of video cameras 50 connected via a video processor 52 to a decision processor 54 which forms part of the system controller 40 and is arranged to analyse the scene around the vehicle 10. Typically, referring back to FIGS. 1 and 2, one camera 50a is mounted on the vehicle cab 14 and arranged to point in a forward direction of the vehicle, one camera 50b is mounted towards the rear of the vehicle, for example on the vertical support section 20a, and arranged to point in a rearward direction of the vehicle, one camera 50c is mounted on the horizontal boom section 20b and arranged to view the gap between the cargo 30 under inspection and the side of the truck 10 nearest to the X-ray source 16 and one camera 50d is also mounted on the horizontal boom section 20b and arranged to view the gap between the cargo 30 and the vertical detector boom section 20c. Additional sensors, including one or more ultrasonic obstacle detectors 51 which have a range of 500 mm to 1000 mm are mounted on the vertical boom section 20c, preferably at different heights, and arranged to provide collision detection around the vertical and horizontal boom sections 20b, 20c. A laser height sensor 53 is mounted towards the top of the vertical boom 20c and arranged to emit a laser light beam around the vertical boom 20c in a horizontal plane just below the level of the underside of the horizontal beam 20b. This is arranged to detect any object under or close to the horizontal beam 20b that is above the height of the laser beam.

Figure 6:
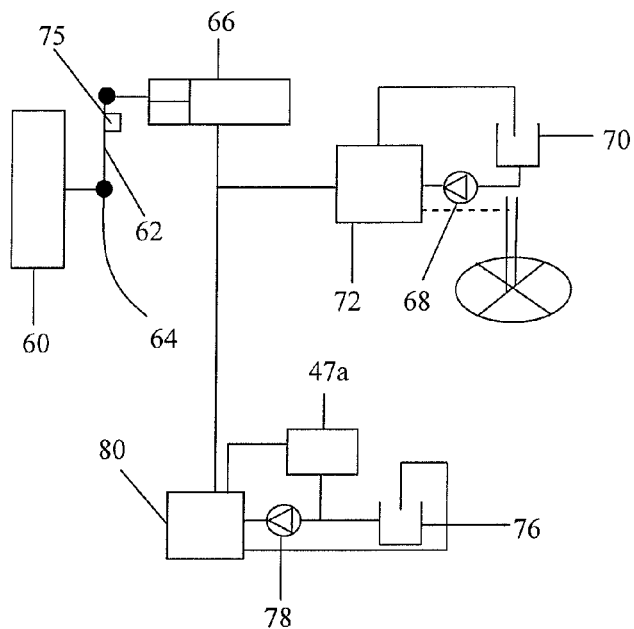
FIG. 6 is a schematic diagram of a steering system of the vehicle of FIG. 1.

Referring to FIG. 6 the steering system of the vehicle 10 includes, for each steerable wheel 60, a track rod 62 which controls the steering angle of the wheel about its pivot axis 64. A hydraulic actuator 66 is arranged to act on the track rod 62 to provide hydraulic control of the steering. A pump 68 provides hydraulic fluid under pressure from a reservoir 70 and a valve system 72 controls the flow of fluid to and from the actuator 66 The valve system 72 is controlled in a known manner in response to turning of the vehicle steering wheel 74 to control the vehicle steering. The system may be a power assisted steering system in which the actuator 66 provides assistance to a mechanical steering input, or it may be a 'steer-by-wire' system in which there is no mechanical link between the steering wheel 74 and the steerable wheel 74 and the steering angle is controlled purely by the actuator 66. A steering angle sensor 75 is arranged to measure the steering angle of the steerable wheel 60 and provide a signal indicative of the steering angle which is used in the steering control.

In order to allow automatic steering of the vehicle by the scan control system, the hydraulic actuator 66 is also connected to a further steering control system comprising a further reservoir 76, pump 78, valve block 80 and the steering control unit 47a. The steering control unit 47a is arranged to control the valve block 80 so as to control the flow of fluid from the reservoir to the actuator 66 and back to the reservoir. The steering control unit 47a receives a signal from the steering sensor 75 indicating the actual steering angle, and a signal from the automatic decision processor indicating a demanded steering angle, and controls the steering angle of the vehicle to the demanded steering angle.

Figure 6A:
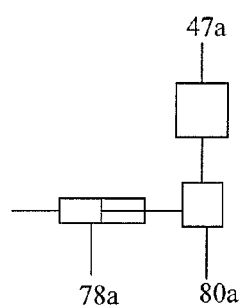
FIG. 6a is a schematic diagram of an alternative steering control system of another embodiment of the invention.

Referring to FIG. 6a, in an alternative arrangement, the secondary steering system comprises a master cylinder 78a connected to the hydraulic steering actuator 66 and an electric actuator 80a arranged to operate the master cylinder under control of the steering control unit 47a. Feedback from the steering sensor 75 can again be input to the steering control unit allowing it to provide a desired steering angle. In this arrangement the range of steering angle can be limited by the size of the master cylinder 78a to be, for example +/−2 degrees, or in some cases up to +/−5 degrees.

In a further alternative arrangement, the steering of the vehicle is electrically controlled using electric motors to control the steering under direct control of the steering control system on the basis of a steering demand signal from a steering wheel sensor and a steering angle signal form a sensor such as the sensor 75 in FIG. 6. In this case the steering controller can comprise a single controller arranged to operate in one mode during normal driving and an automatic scan mode during scanning.

Figure 7:
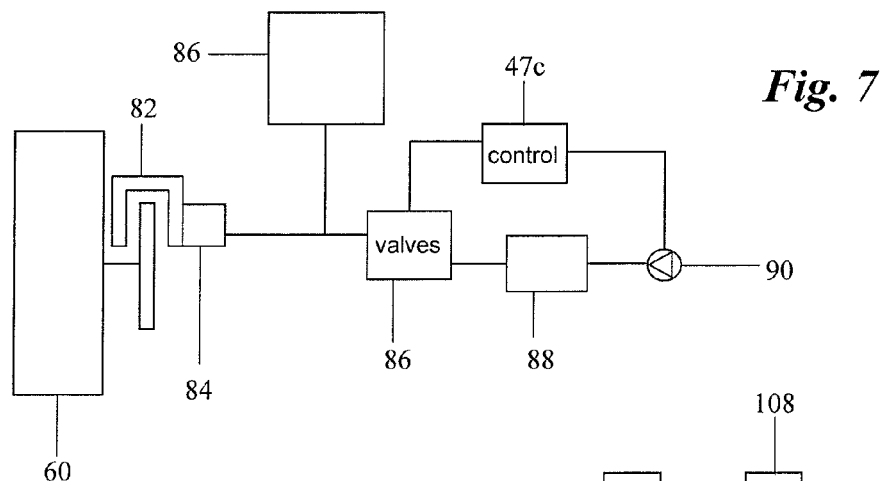
FIG. 7 is a schematic diagram of a braking system of the vehicle of FIG. 1.

Referring to FIG. 7, the braking system of the vehicle 10 comprises for each wheel 60 brake 82 operated by a pneumatic actuator 84. The normal brake control system 86 controls the air pressure to the actuator 84 under normal operation. The actuator 84 is further connected via a valve block 86 to a pneumatic reservoir 88 which receives air under pressure from a compressor 90. The brake control unit 47c controls operation of the valve block 86 and the compressor 90 to control actuation of the brakes under control of the automatic decision processor 54.

Figure 8:
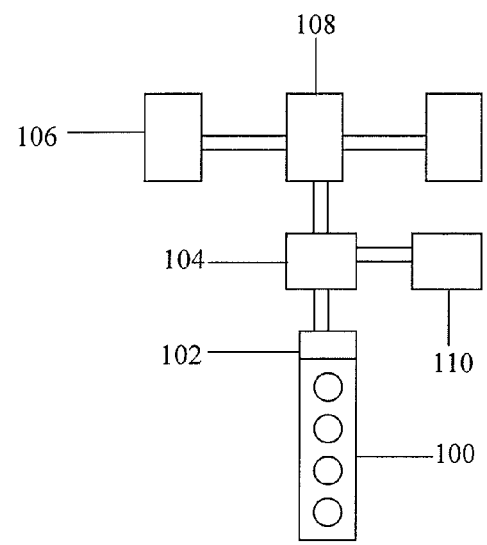
FIG. 8 is a schematic view of the drive train of the vehicle of FIG. 1.

Referring to FIG. 8, the drive train of the vehicle 10 comprises an engine 100, a primary gear box 102 connected to the output crankshaft of the engine 100, a secondary gear box 104 connected to the output of the primary gearbox 102 and arranged to provide drive to the driven wheels 106 via a differential 108. The secondary gearbox 104 is also connected to a drive motor 110 and is arranged to disconnect the main gear box from the differential and connect the drive motor to the differential when the vehicle is to be controlled by the scanning system. When the vehicle is under normal use the secondary gear box 104 is arranged to disconnect the drive motor 110 and connect the primary gear box 102 to the differential. The drive train control unit 47b is arranged to control the secondary gear box 104 and the motor 110, under control of the automatic decision processor 54, to control the speed of the vehicle during an automatic scan operation. The motor 110 and secondary gear box 104 can be arranged to provide vehicle speeds only up to 2 m/s, or in some cases only up to 1 m/s.

In order to perform a scan, the vehicle 10 is lined up approximately with the item 30 to be scanned, so that the item is located to the side of the vehicle 10 in front of the boom 20. The driver then leaves the vehicle and the exclusion zone 32. When the scan is to be started, the start signal is sent from the control station 40a. On receipt of this signal, the automatic scan process is started. Before the vehicle is moved, and while it is moving, image data from the video cameras 50 (and other collision detect sensors that may be installed) is passed through to the video processor 52. The video processor 52 compresses the image data by extracting the most relevant information into a set of feature vectors that can then be passed to the automatic decision processor 54. Examples of feature vectors include the set of binary collision detector outputs, the clearance distances between the object 30 under inspection and the vertical detector boom 20c as a function of angle around the centre of the boom (i.e. the rotational axis of the horizontal boom section 20b), the distance to the end of scan and the distance clear ahead of the vehicle.

The set of feature vectors that are generated by the video processor 52 are then passed to the automatic decision processor 54. The automatic decision processor 54 analyses the feature vectors to determine whether the scan can be started. For example this may include determining whether the nearest object is no less than a predetermined minimum distance in front of the scanner plane, so that the vehicle can reach a desired constant speed for scanning before the scanning of the item begins. It can also be arranged to determine the orientation of the object to be scanned, and determine whether it is closely enough aligned with the vehicle, both in its orientation and in its position in the lateral direction of the vehicle, for the scan to be completed using only the limited steering angle provided by the automatic steering system. This can help to prevent the scan being started and then subsequently abandoned. If the scan has started, the decision processor 54 determines whether it can be continued, or whether an obstruction is likely to be reached, in which case the vehicle is stopped. The automatic decision processor 54 also analyses the direction in which the vehicle 10 is steering and calculates the necessary modification to vehicle trajectory required to maintain at least a minimum spacing between the vehicle 10 and the scanned item, and the vertical boom section 20c and the scanned item during the scan. Finally the automatic decision processor 54 determines when the scan should be stopped by analysing video data from the forward and rearward pointing cameras 50, from the other sensors 50, 51, 53, and from the X-ray data itself. For example, if no object is present in the X-ray beam and there are no further cargo items to scan indicated in the feature vectors from the cameras, then the scan can be stopped.

The automatic decision processor 54 has a direct link to vehicle systems 47, as described above, including the vehicle steering control unit 47a and the control unit 47b for the vehicle drive system and a braking control unit 47c for the vehicle brakes. The automatic decision processor 54 also monitors vehicle velocity, which for example can be indicated to it on a continuous basis by the vehicle drive system control unit 47b, to ensure stable imaging characteristics.

In a modification to this embodiment the operator inputs 40a are arranged to control the control station 40a to transmit a vehicle speed signal indicative of a desired speed of the vehicle and a vehicle steering signal indicative of a desired steering angle of the vehicle. These signals are communicated to the system controller 40 which is arranged to receive them and to control the vehicle drive system, steering system and braking system so as to achieve the desired speed and steering angle. This enables the operator to control the speed and steering of the vehicle by remote control from the control station 40a. This may be used throughout the whole scan, or for initial alignment of the vehicle with the item to be scanned before switching to an automatic scanning mode. In this remote control mode, the system controller 40 will monitor the signals from the sensors and stop the vehicle if it is about to hit an obstacle.

A set of safety circuits measure the truck systems to ensure that all aspects of the system are stable and under control at all time. The safety system also use the images from the video cameras 50 and the signals from the ultrasonic and laser sensors, for example by monitoring a set of feature vectors that are generated by the automatic decision processor, to determine whether predetermined safety conditions are met which indicate that personnel are located with the safety exclusion zone. The safety systems are arranged to cause termination of X-ray exposure and mechanical scanning movement of the truck if a safety condition is broached.

As described in our UK patent application No. 0803644.4, which is incorporated herein by reference in its entirety, the image data which is produced from the standalone truck system can be passed into a network of operator workstations which may be physically remote from the scanning area. The image data can be dispatched to an available operator for review together with video images of the cargo item under inspection and other relevant data such as cargo manifest information.

The invention claimed is:

1. A mobile scanning system comprising:
   a vehicle;
   a scanner, including a radiation source and detection means mounted on the vehicle and arranged to scan an object and define a scanner plane,
   control means mounted on the vehicle and arranged to control the scanner,
   an operator system arranged to be located remote from the vehicle and to communicate with the control means to enable an operator to interact remotely with the control means;
   a video camera positioned on the vehicle for capturing a plurality of images and a video processor for processing said plurality of images and producing a plurality of feature vectors;
   a decision processor for analyzing said plurality of feature vectors to determine whether an object is no less than a predetermined distance in front of the scanner plane such that the vehicle can reach a desired constant speed for scanning before a scan of the object begins; and
   a drive train arrange to drive wheels of the vehicle, wherein the drive train comprises an engine, a primary gear box connected to an output crankshaft of the engine, a secondary gear box connected to an output of the primary gearbox, and a differential connected to the secondary gear box, wherein the secondary gear box is arranged to provide drive to the wheels via the differential, is connected to a drive motor, and is arranged to disconnect the primary gear box from the differential and connect the drive motor to the differential in response to the control means.

2. A system according to claim 1 wherein the operator system is arranged to communicate wirelessly with the control means.

3. A system according to claim 1 wherein the scanner is arranged to generate scan data when scanning an object, and the control means is arranged to communicate the scan data to a monitoring system.

4. A system according to claim 3 wherein the monitoring system is arranged to generate an image from the scan data.

5. A system according to claim 4 wherein the monitoring system includes display means arranged to display the image to an operator.

6. A system according to claim 3 wherein the monitoring system is remote from the operator system.

7. A system according to claim 3 wherein the monitoring system forms part of the operator system.

8. A system according to claim 1 wherein the control means is arranged to receive signals from the operator system and to control the scanner in response to the signals.

9. A system according to claim 1 wherein the control means is arranged to receive signals from the operator system and to control the vehicle in response to the signals.

10. A system according to claim 1 further comprising sensing means wherein the control means is arranged to control the scanner in response to signals from the sensing means.

11. A system according to claim 10 wherein the control means is arranged to identify an object within a scanning path of the scanner and to control the scanner depending on the nature of the object.

12. A system according to claim 1 further comprising sensing means wherein the control means is arranged to control the vehicle in response to signals from the sensing means.

13. A system according to claim 12 wherein the control means is arranged to identify obstacles using signals from the sensing means and to control the vehicle to avoid any detected obstacles.

14. A system according to claim 8 wherein the control means is arranged to control at least one of starting and stopping of the scanner in response to the signals.

15. A system according to claim 7 wherein the control means is arranged to control at least one of the speed and steering of the vehicle in response to the signals.

16. A system according to claim 1 further including a scanner support system arranged to support at least a part of the scanner on the vehicle, wherein the control means is arranged to control the scanner support system.

17. A system according to claim 16 wherein the control means is arranged to control the scanner support system in response to signals from at least one of the operator system and sensing means.

18. A system according to claim 1 wherein, when the vehicle is not in scanning mode, the secondary gear box is arranged to disconnect the drive motor and connect the primary gear box to the differential.

19. A system according to claim 1 further comprising an automatic decision processor wherein the automatic decision processor controls the secondary gear box and the motor to control a speed of the vehicle during a scan operation.

* * * * *